(12) United States Patent
Schlameuss et al.

(10) Patent No.: US 12,057,220 B2
(45) Date of Patent: *Aug. 6, 2024

(54) SYSTEMS AND METHODS FOR MANAGING BUILDING WELLNESS

(71) Applicant: View Operating Corporation, Milpitas, CA (US)

(72) Inventors: Eric Schlameuss, Stamford, CT (US); Michael Aisner, New Rochelle, NY (US); Paul Rode, Tarrytown, NY (US); Greg Zimerman, Brooklyn, NY (US); Cory Gordon Clarke, Yonkers, NY (US); Scott Rechler, Old Brookville, NY (US); Francis Pusinelli, Hicksville, NY (US)

(73) Assignee: View Operating Corporation, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/115,694

(22) Filed: Feb. 28, 2023

(65) Prior Publication Data
US 2023/0230686 A1 Jul. 20, 2023

Related U.S. Application Data

(63) Continuation of application No. 17/328,346, filed on May 24, 2021, now Pat. No. 11,631,493.
(Continued)

(51) Int. Cl.
*G16H 40/20* (2018.01)
*G01N 33/18* (2006.01)
(Continued)

(52) U.S. Cl.
CPC ............. *G16H 40/20* (2018.01); *G01N 33/18* (2013.01); *G05B 15/02* (2013.01);
(Continued)

(58) Field of Classification Search
CPC ........ G16H 40/20; G16H 10/60; G16H 15/00; G16H 50/30; G01N 33/18; G05B 15/02;
(Continued)

(56) References Cited

U.S. PATENT DOCUMENTS

| | | |
|---|---|---|
| 4,340,813 A | 7/1982 | Sauer |
| 5,729,824 A | 3/1998 | O'Neill et al. |

(Continued)

FOREIGN PATENT DOCUMENTS

| | | |
|---|---|---|
| AU | 2015101660 A4 | 12/2015 |
| CN | 103119845 A | 5/2013 |

(Continued)

OTHER PUBLICATIONS

Alarifi, A. et al., "Ultra Wideband Indoor Positioning Technologies: Analysis and Recent Advances", Sensors, May 16, 2016, vol. 16 No. 5, pp. 1-36.

(Continued)

*Primary Examiner* — Eliza A Lam
(74) *Attorney, Agent, or Firm* — Weaver Austin Villeneuve & Sampson LLP; Brian D. Griedel

(57) ABSTRACT

A system and a computer-implemented method of managing building wellness. The method may include the steps of: obtaining wellness parameters for a building (e.g., an office building) having an occupant(s); processing the wellness parameter to determine a current wellness index for the building and, based on the current wellness index, sending a message regarding the current wellness index to a recipient(s) (e.g., a building occupant), displaying the current wellness index for a user(s), and/or identifying a remediation action(s) to improve the current wellness index.

20 Claims, 2 Drawing Sheets

Related U.S. Application Data

(60) Provisional application No. 63/030,507, filed on May 27, 2020.

(51) Int. Cl.

| | |
|---|---|
| *G05B 15/02* | (2006.01) |
| *G06Q 10/0635* | (2023.01) |
| *G06Q 10/105* | (2023.01) |
| *G06Q 50/163* | (2024.01) |
| *G06Q 50/26* | (2024.01) |
| *G16H 10/60* | (2018.01) |
| *G16H 15/00* | (2018.01) |
| *G16H 50/30* | (2018.01) |

(52) U.S. Cl.
CPC ....... *G06Q 10/0635* (2013.01); *G06Q 10/105* (2013.01); *G16H 10/60* (2018.01); *G16H 15/00* (2018.01); *G16H 50/30* (2018.01); *G06Q 50/163* (2013.01); *G06Q 50/26* (2013.01)

(58) Field of Classification Search
CPC ............. G06Q 10/0635; G06Q 10/105; G06Q 50/163; G06Q 50/26; Y02A 90/10
See application file for complete search history.

(56) References Cited

U.S. PATENT DOCUMENTS

| | | | |
|---|---|---|---|
| 6,104,513 | A | 8/2000 | Bloom |
| 6,588,250 | B2 | 7/2003 | Schell |
| 6,897,936 | B1 | 5/2005 | Li et al. |
| 6,965,813 | B2 | 11/2005 | Granqvist et al. |
| 7,031,727 | B2 | 4/2006 | Baskin |
| 7,111,952 | B2 | 9/2006 | Veskovic |
| 7,310,355 | B1 | 12/2007 | Krein et al. |
| 7,382,636 | B2 | 6/2008 | Baarman et al. |
| 7,554,437 | B2 | 6/2009 | Axelsen |
| 7,588,067 | B2 | 9/2009 | Veskovic |
| 7,629,400 | B2 | 12/2009 | Hyman |
| 7,911,348 | B2 | 3/2011 | Rodgers |
| 7,950,827 | B2 | 5/2011 | Veskovic |
| 7,963,675 | B2 | 6/2011 | Veskovic |
| 8,022,977 | B2 | 9/2011 | Kanade et al. |
| 8,086,433 | B2 | 12/2011 | Lee et al. |
| 8,249,731 | B2 | 8/2012 | Tran et al. |
| 8,705,162 | B2 | 4/2014 | Brown et al. |
| 8,711,465 | B2 | 4/2014 | Bhatnagar et al. |
| 8,927,069 | B1 | 1/2015 | Estinto et al. |
| 9,121,837 | B2 | 9/2015 | Chan et al. |
| 9,551,913 | B2 | 1/2017 | Kim et al. |
| 9,715,242 | B2 | 7/2017 | Pillai et al. |
| 9,898,912 | B1 | 2/2018 | Jordan, II et al. |
| 9,930,463 | B2 | 3/2018 | Little |
| 9,965,865 | B1 | 5/2018 | Agrawal et al. |
| 10,156,852 | B2 | 12/2018 | Bakhishev et al. |
| 10,178,638 | B1 | 1/2019 | Stamatakis et al. |
| 10,289,094 | B2 | 5/2019 | Ashdown et al. |
| 10,322,680 | B2 | 6/2019 | Terashima et al. |
| 10,488,837 | B2 | 11/2019 | Cirino |
| 10,724,867 | B1 | 7/2020 | Waful et al. |
| 10,867,266 | B1 | 12/2020 | Carlin et al. |
| 10,917,259 | B1 | 2/2021 | Chein et al. |
| 10,921,675 | B2 | 2/2021 | Barnum et al. |
| 10,923,226 | B2 | 2/2021 | Macary et al. |
| 10,954,677 | B1 | 3/2021 | Scanlin |
| 10,982,487 | B2 | 4/2021 | Ramirez |
| 11,182,970 | B1 | 11/2021 | Kathol |
| 11,631,493 | B2 | 4/2023 | Schlameuss et al. |
| 11,743,071 | B2 | 8/2023 | Trikha et al. |
| 11,822,159 | B2 | 11/2023 | Brown et al. |
| 2001/0042976 | A1 | 11/2001 | Breed et al. |
| 2003/0039257 | A1 | 2/2003 | Manis et al. |
| 2003/0163351 | A1 | 8/2003 | Brown et al. |
| 2003/0227663 | A1 | 12/2003 | Agrawal et al. |
| 2005/0002662 | A1 | 1/2005 | Arpa et al. |
| 2005/0046584 | A1 | 3/2005 | Breed |
| 2005/0063036 | A1 | 3/2005 | Bechtel et al. |
| 2005/0157675 | A1 | 7/2005 | Feder et al. |
| 2005/0213992 | A1 | 9/2005 | Piehler |
| 2006/0074494 | A1 | 4/2006 | McFarland |
| 2006/0270440 | A1 | 11/2006 | Shearer et al. |
| 2007/0008603 | A1 | 1/2007 | Sotzing et al. |
| 2007/0067048 | A1 | 3/2007 | Bechtel et al. |
| 2007/0191074 | A1 | 8/2007 | Harrist et al. |
| 2007/0222542 | A1 | 9/2007 | Joannopoulos et al. |
| 2008/0088821 | A1 | 4/2008 | Hurvitz et al. |
| 2008/0182506 | A1 | 7/2008 | Jackson et al. |
| 2008/0277486 | A1 | 11/2008 | Seem et al. |
| 2009/0210252 | A1 | 8/2009 | Silver |
| 2009/0231662 | A1 | 9/2009 | Sorensson et al. |
| 2009/0322347 | A1 | 12/2009 | Hashimshony et al. |
| 2010/0188057 | A1 | 7/2010 | Tarng |
| 2010/0243427 | A1 | 9/2010 | Kozlowski et al. |
| 2010/0245973 | A1 | 9/2010 | Wang et al. |
| 2010/0315693 | A1 | 12/2010 | Lam et al. |
| 2011/0050756 | A1 | 3/2011 | Cassidy et al. |
| 2011/0148218 | A1 | 6/2011 | Rozbicki |
| 2011/0266137 | A1 | 11/2011 | Wang et al. |
| 2011/0266138 | A1 | 11/2011 | Wang et al. |
| 2011/0267674 | A1 | 11/2011 | Wang et al. |
| 2011/0267675 | A1 | 11/2011 | Wang et al. |
| 2011/0310519 | A1 | 12/2011 | Baba et al. |
| 2012/0032855 | A1 | 2/2012 | Reede et al. |
| 2012/0033287 | A1 | 2/2012 | Friedman et al. |
| 2012/0039526 | A1 | 2/2012 | Garaas et al. |
| 2012/0062975 | A1 | 3/2012 | Mehtani et al. |
| 2012/0112883 | A1 | 5/2012 | Wallace et al. |
| 2012/0133315 | A1 | 5/2012 | Berman et al. |
| 2012/0143516 | A1 | 6/2012 | Mezic et al. |
| 2012/0239209 | A1 | 9/2012 | Brown et al. |
| 2012/0296610 | A1 | 11/2012 | Hailemariam et al. |
| 2013/0057937 | A1 | 3/2013 | Berman et al. |
| 2013/0073681 | A1 | 3/2013 | Jiang et al. |
| 2013/0130227 | A1 | 5/2013 | Peltz et al. |
| 2013/0226353 | A1 | 8/2013 | Park |
| 2013/0250422 | A1 | 9/2013 | Tandler |
| 2013/0271814 | A1 | 10/2013 | Brown |
| 2013/0277539 | A1 | 10/2013 | Smilansky et al. |
| 2013/0306615 | A1 | 11/2013 | Rozbicki et al. |
| 2014/0007244 | A1 | 1/2014 | Martin et al. |
| 2014/0028551 | A1 | 1/2014 | Ruff et al. |
| 2014/0101573 | A1 | 4/2014 | Kuo |
| 2014/0236323 | A1 | 8/2014 | Brown et al. |
| 2014/0247475 | A1 | 9/2014 | Parker et al. |
| 2014/0300945 | A1 | 10/2014 | Parker |
| 2014/0317514 | A1 | 10/2014 | Bokotey |
| 2014/0368899 | A1 | 12/2014 | Greer |
| 2015/0032264 | A1 | 1/2015 | Emmons et al. |
| 2015/0070745 | A1 | 3/2015 | Pradhan |
| 2015/0106121 | A1 | 4/2015 | Muhsin et al. |
| 2015/0116811 | A1 | 4/2015 | Shrivastava et al. |
| 2015/0122474 | A1 | 5/2015 | Petersen |
| 2015/0195644 | A1 | 7/2015 | Wilson et al. |
| 2015/0255651 | A1 | 9/2015 | Barr et al. |
| 2015/0270823 | A1 | 9/2015 | Sobolewski |
| 2015/0323915 | A1 | 11/2015 | Warren et al. |
| 2015/0327010 | A1 | 11/2015 | Gottschalk et al. |
| 2015/0362819 | A1 | 12/2015 | Bjornard et al. |
| 2015/0378715 | A1 | 12/2015 | Solnit et al. |
| 2016/0027391 | A1 | 1/2016 | Gibson et al. |
| 2016/0071183 | A1 | 3/2016 | Joshi et al. |
| 2016/0091769 | A1 | 3/2016 | Rozbicki |
| 2016/0134932 | A1 | 5/2016 | Karp et al. |
| 2016/0210711 | A1 | 7/2016 | Krupa et al. |
| 2016/0231755 | A1 | 8/2016 | Ajax et al. |
| 2016/0261837 | A1 | 9/2016 | Thompson et al. |
| 2016/0376831 | A1 | 12/2016 | Plummer |
| 2017/0010880 | A1 | 1/2017 | Yamazaki |
| 2017/0039339 | A1 | 2/2017 | Bitran et al. |
| 2017/0075183 | A1 | 3/2017 | Brown |
| 2017/0080341 | A1 | 3/2017 | Mao et al. |
| 2017/0082903 | A1 | 3/2017 | Vigano et al. |

(56) References Cited

U.S. PATENT DOCUMENTS

| | | |
|---|---|---|
| 2017/0085834 A1 | 3/2017 | Kim et al. |
| 2017/0086003 A1 | 3/2017 | Rabinowitz et al. |
| 2017/0122802 A1 | 5/2017 | Brown et al. |
| 2017/0146884 A1 | 5/2017 | Vigano et al. |
| 2017/0161911 A1 | 6/2017 | Kumar et al. |
| 2017/0248564 A1 | 8/2017 | Miyajima |
| 2017/0264865 A1 | 9/2017 | Huangfu |
| 2017/0276542 A1 | 9/2017 | Klawuhn et al. |
| 2017/0345267 A1 | 11/2017 | Flint et al. |
| 2017/0374255 A1 | 12/2017 | Campbell et al. |
| 2017/0374437 A1 | 12/2017 | Schwarzkopf et al. |
| 2018/0090992 A1 | 3/2018 | Shrivastava et al. |
| 2018/0119973 A1 | 5/2018 | Rothman et al. |
| 2018/0129172 A1 | 5/2018 | Shrivastava et al. |
| 2018/0130455 A1 | 5/2018 | Plummer et al. |
| 2018/0139517 A1 | 5/2018 | Schwartz et al. |
| 2018/0144696 A1 | 5/2018 | Zhang et al. |
| 2018/0153454 A1 | 6/2018 | Hayter et al. |
| 2018/0156484 A1 | 6/2018 | Kim et al. |
| 2018/0181085 A1 | 6/2018 | Gabriel et al. |
| 2018/0187484 A1 | 7/2018 | Hebeisen et al. |
| 2018/0195752 A1 | 7/2018 | Sasaki et al. |
| 2018/0225585 A1 | 8/2018 | Dong et al. |
| 2018/0259373 A1 | 9/2018 | Staton et al. |
| 2018/0269974 A1 | 9/2018 | Luciano |
| 2018/0306609 A1 | 10/2018 | Agarwal et al. |
| 2018/0307114 A1 | 10/2018 | Brown et al. |
| 2018/0321042 A1 | 11/2018 | Brewer et al. |
| 2018/0349710 A1 | 12/2018 | Houri et al. |
| 2018/0364654 A1 | 12/2018 | Locke et al. |
| 2019/0025661 A9 | 1/2019 | Brown et al. |
| 2019/0049812 A1 | 2/2019 | Brown |
| 2019/0058977 A1 | 2/2019 | Gherardi et al. |
| 2019/0097827 A1 | 3/2019 | Angle et al. |
| 2019/0178511 A1 | 6/2019 | Zimmerman et al. |
| 2019/0205774 A1 | 7/2019 | Ba et al. |
| 2019/0229768 A1 | 7/2019 | Jeremy et al. |
| 2019/0257143 A1 | 8/2019 | Nagel et al. |
| 2019/0317458 A1 | 10/2019 | Shrivastava et al. |
| 2019/0324431 A1 | 10/2019 | Cella et al. |
| 2019/0346417 A1 | 11/2019 | Benefield |
| 2019/0354071 A1 | 11/2019 | Turney et al. |
| 2019/0356508 A1 | 11/2019 | Trikha et al. |
| 2020/0026141 A1 | 1/2020 | Brown et al. |
| 2020/0033163 A1 | 1/2020 | Agarwal et al. |
| 2020/0041967 A1 | 2/2020 | Shrivastava et al. |
| 2020/0045261 A1 | 2/2020 | Lim et al. |
| 2020/0090089 A1 | 3/2020 | Aston et al. |
| 2020/0096775 A1 | 3/2020 | Franklin et al. |
| 2020/0103841 A1 | 4/2020 | Pillai et al. |
| 2020/0176125 A1 | 6/2020 | Chatterjea et al. |
| 2020/0193155 A1 | 6/2020 | Keohane et al. |
| 2020/0200416 A1* | 6/2020 | Granger ................. G16H 40/67 |
| 2020/0227159 A1 | 7/2020 | Boisvert et al. |
| 2021/0021788 A1 | 1/2021 | Mcnelley et al. |
| 2021/0063836 A1 | 3/2021 | Patterson et al. |
| 2021/0132458 A1 | 5/2021 | Trikha et al. |
| 2021/0210053 A1 | 7/2021 | Ng et al. |
| 2021/0225528 A1 | 7/2021 | Viengkham et al. |
| 2021/0375440 A1 | 12/2021 | Schlameuss et al. |
| 2021/0383804 A1 | 12/2021 | Makker et al. |
| 2021/0390953 A1 | 12/2021 | Makker et al. |
| 2022/0044673 A1 | 2/2022 | Park et al. |
| 2022/0231396 A1 | 7/2022 | Rozbicki et al. |
| 2023/0040424 A1 | 2/2023 | Gopinathanasari et al. |
| 2023/0065864 A1 | 3/2023 | Trikha et al. |
| 2023/0074720 A1 | 3/2023 | Brown et al. |
| 2023/0152652 A1 | 5/2023 | Trikha et al. |
| 2023/0176669 A1 | 6/2023 | Gupta et al. |
| 2023/0194115 A1 | 6/2023 | Malik et al. |
| 2023/0288770 A1 | 9/2023 | Gupta et al. |
| 2023/0333434 A1 | 10/2023 | Gupta et al. |
| 2023/0353416 A1 | 11/2023 | Trikha et al. |
| 2023/0367584 A1 | 11/2023 | Tai et al. |
| 2024/0085754 A1 | 3/2024 | Martinson et al. |

FOREIGN PATENT DOCUMENTS

| | | |
|---|---|---|
| CN | 203019761 U | 6/2013 |
| CN | 103649826 A | 3/2014 |
| CN | 106125442 A | 11/2016 |
| CN | 106364442 A | 2/2017 |
| CN | 110515425 A | 11/2019 |
| EP | 0917667 A1 | 5/1999 |
| EP | 2090961 A1 | 8/2009 |
| EP | 3299957 A1 | 3/2018 |
| EP | 3328000 A1 | 5/2018 |
| JP | H0611477 A | 1/1994 |
| JP | H06308073 A | 11/1994 |
| KR | 20120092921 A | 8/2012 |
| KR | 20170121858 A | 11/2017 |
| KR | 20170134321 A | 12/2017 |
| KR | 20180012615 A | 2/2018 |
| KR | 101853568 B1 | 4/2018 |
| TW | I607269 B | 12/2017 |
| WO | WO-02054086 A1 | 7/2002 |
| WO | WO-2013121103 A1 | 8/2013 |
| WO | WO-2014032023 A1 | 2/2014 |
| WO | WO-2014209812 A1 | 12/2014 |
| WO | WO-2015100419 A1 | 7/2015 |
| WO | WO-2015113592 A1 | 8/2015 |
| WO | WO-2016054112 A1 | 4/2016 |
| WO | WO-2016072620 A1 | 5/2016 |
| WO | WO-2016085964 A1 | 6/2016 |
| WO | WO-2017007841 A1 | 1/2017 |
| WO | WO-2017058568 A1 | 4/2017 |
| WO | WO-2017075472 A1 | 5/2017 |
| WO | WO-2017120262 A1 | 7/2017 |
| WO | WO-2017182920 A1 * | 10/2017 |
| WO | WO-2017189618 A1 | 11/2017 |
| WO | WO-2017192881 A1 | 11/2017 |
| WO | WO-2018039080 A1 | 3/2018 |
| WO | WO-2018063919 A1 | 4/2018 |
| WO | WO-2018102103 A1 | 6/2018 |
| WO | WO-2018200702 A1 | 11/2018 |
| WO | WO-2018200740 A2 | 11/2018 |
| WO | WO-2018200752 A1 | 11/2018 |
| WO | WO-2019178282 A1 | 9/2019 |
| WO | WO-2019213441 A1 | 11/2019 |
| WO | WO-2020146766 A1 | 7/2020 |
| WO | WO-2020243690 A1 | 12/2020 |
| WO | WO-2021211798 A1 | 10/2021 |

OTHER PUBLICATIONS

Chan, E.C.L., et al., "Effect of Channel Interference on Indoor Wireless Local Area Network Positioning" IEEE 6th International Conference on Wireless and Mobile Computing, Networking and Communications, Oct. 11, 2010, pp. 239-245.

CN Office Action dated Mar. 2, 2022 in Application No. CN201980042340.1 with English translation.

CN Office Action dated Nov. 2, 2022, in ApplicationNo. CN201980042340.1 with English translation.

Density DPU Technical Specifications v1.0, Density, 2018, downloaded from www.density.io.

Dols, W. Stuart, et al., A tool to model the fate and transport of indoor microbiological aerosols (FaTIMA), NIST Technical Note 2095, National Institute of Standards and Technology, US Department of Commerce, Jun. 2020, 32 pp. https://doi.org/10.6028/NIST.TN.2095.

EP Office action dated Jan. 10, 2022, in Application No. EP19745809.4.

"Halio Rooftop Sensor Kit (Model SR500)," Product Data Sheet, Kinestral Technologies, 2020, 4 pp.

International Preliminary Report on Patentability and written opinion dated Jul. 21, 2022 in Application PCT/US2021/012313.

International Preliminary Report on Patentability dated Oct. 6, 2022 in PCT Application PCT/US2021/023433.

International Search Report and Written Opinion dated Aug. 2, 2022 in Application No. PCT/US2022/030757.

International Search Report and Written Opinion dated Aug. 22, 2022 in Application No. PCT/US2022/024343.

(56) References Cited

OTHER PUBLICATIONS

International Search Report and Written Opinion dated Mar. 25, 2022 in Application No. PCT/US2021/062774.
International Search Report and Written Opinion dated Sep. 26, 2022 in Application No. PCT/US2022/032993.
International Preliminary Report on Patentability dated Apr. 13, 2023 in PCT Application No. No. PCT/US2021/052587.
International Preliminary Report on Patentability dated Aug. 11, 2022 in PCT Application No. PCT/US2021/015378.
International Preliminary Report on Patentability dated Dec. 1, 2022, in PCT Application No. PCT/US2021/033544.
International Preliminary Report on Patentability dated Dec. 9, 2021, in PCT Application No. PCT/US2020/035485.
International Preliminary Report on Patentability dated Dec. 22, 2020 in PCT/US2019/038429.
International Preliminary Report on Patentability dated Feb. 9, 2023 in PCT Application No. PCT/US2021/043143.
International Preliminary Report on Patentability dated Mar. 9, 2023 in PCT Application No. PCT/US2021/046838.
International Search Report and Written Opinion dated Aug. 8, 2022, in Application No. PCT/US2022/023605.
International Search Report and Written Opinion dated Jan. 17, 2022 in PCT Application No. PCT/US2021/046838.
International Search Report and Written Opinion dated Jul. 6, 2022, in PCT Application No. PCT/US2022/020730.
International Search Report and Written Opinion dated Jun. 23, 2021 in PCT Application No. PCT/US2021/015378.
International Search Report and Written Opinion dated Mar. 8, 2022 in PCT Application No. PCT/US2021/052587.
International Search Report and Written Opinion dated Nov. 10, 2021 in PCT Application No. PCT/US2021/043143.
International Search Report and Written Opinion dated Sep. 1, 2022, in Application No. PCT/US2022/024812.
International Search Report and Written Opinion dated Sep. 3, 2021 in PCT Application No. PCT/US2021/033544.
International Search Report and Written Opinion dated Sep. 16, 2019 in PCT/US2019/038429.
International Search Report and Written Opinion (ISA/EP) dated Sep. 30, 2020 in PCT Application No. PCT/US2020/035485.
Joseph, J., "Xiaomi shows off near perfect Under Screen Camera Technology," Gizchina.com, Aug. 28, 2020, 7 pp., " title="Link: https://www.gizmochina.com/2020/08/28/xiaomi-perfected-third-gen-under-screen-camera-technology-prototype/>">https://www.gizmochina.com/2020/08/28/xiaomi-perfected-third-gen-under-screen-camera-technology-prototype/ , retrieved Apr. 21, 2021.
JP Office Action dated Dec. 20, 2022 in JP Application No. JP2020-570981 with English translation.
PCT Application No. PCT/US2021/012313 filed Jan. 6, 2021.
PCT Application No. PCT/US2021/015378 filed Jan. 28, 2021.
PCT Application No. PCT/US2021/023433 filed Mar. 23, 2021.
PCT Application No. PCT/US2021/030798 filed May 5, 2021.
PCT Application No. PCT/US2021/052587 filed Sep. 29, 2021.
"SPN1 Sunshine Pyranometer," Product Overview, Specification, Accessories and Product Resources, Delta-T Devices, May 5, 2016, 9 pp. https://www.delta-t.co.uk/product/spn1/ (downloaded Apr. 28, 2020).
TW Office Action dated Feb. 16, 2023, in Application No. TW108121734 with English translation.
TW Office Action dated Jul. 14, 2022, in Application No. TW108121734 with English translation.
TW Office Action dated Mar. 15, 2022, in Application No. TW109112242 with English translation.
U.S Advisory Action dated Aug. 31, 2022 in U.S. Appl. No. 16/447,169.
U.S. Advisory Action dated Apr. 29, 2022 in U.S. Appl. No. 17/328,346.
U.S. Advisory Action dated Dec. 15, 2021 in U.S. Appl. No. 16/447,169.
U.S Advisory Action dated Jan. 22, 2023 in U.S. Appl. No. 16/550,052.
U.S. Appl. No. 62/958,653, inventors Gopinathanasari et al., filed on Jan. 8, 2020.
U.S. Appl. No. 62/993,617, inventors Gupta et al., filed on Mar. 23, 2020.
U.S. Appl. No. 63/020,819, inventors Gupta et al., filed on May 6, 2020.
U.S. Appl. No. 63/029,301, inventors Gupta et al., filed on May 22, 2020.
U.S. Appl. No. 63/033,474, inventors Gupta et al., filed on Jun. 2, 2020.
U.S. Appl. No. 63/034,792, inventors Gupta et al., filed on Jun. 4, 2020.
U.S. Appl. No. 63/041,002, inventors Gupta et al., filed on Jun. 18, 2020.
U.S. Appl. No. 63/057,120, Inventors Gupta et al., filed on Jul. 27, 2020.
U.S. Appl. No. 63/069,358, inventors Gupta et al., filed on Aug. 24, 2020.
U.S. Appl. No. 63/078,805, Inventors Gupta et al., filed on Sep. 15, 2020.
U.S. Appl. No. 63/079,851, inventors Gupta et al., filed on Sep. 17, 2020.
U.S. Appl. No. U.S. Appl. No. 63/106,058, inventors Rasmus-Vorrath et al., filed on Oct. 27, 2020.
U.S. Appl. No. 63/115,886, Inventors Gupta et al., filed on Nov. 19, 2020.
U.S. Appl. No. 63/133,725, inventors Gopinathanasari et al., filed on Jan. 4, 2021.
U.S. Appl. No. 63/159,814, Inventors Gupta et al., filed on Mar. 11, 2021.
U.S. Appl. No. 63/173,759, inventors Rasmus-Vorrath et al., filed on Apr. 12, 2021.
U.S. Appl. No. 63/209,362, Inventors Gomez-Martinez et al., filed on Jun. 10, 2021.
U.S. Appl. No. 63/233,122, inventors Gupta et al., filed on Aug. 13, 2021.
US Final Office Action dated Aug. 13, 2021 in U.S. Appl. No. 16/447,169.
U.S. Final office Action dated Dec. 1, 2021 in U.S. Appl. No. 17/328,346.
U.S. Final Office Action dated Dec. 2, 2022 in U.S. Appl. No. 16/550,052.
US Final Office Action dated Jan. 1, 2021 in U.S. Appl. No. 16/550,052.
U.S. Final Office Action dated Jun. 24, 2022, in U.S. Appl. No. 16/447,169.
US Final Office Action dated Oct. 28, 2021 in U.S. Appl. No. 16/550,052.
U.S. Non Final office Action dated Sep. 2, 2021 in U.S. Appl. No. 17/328,346.
U.S. Non-Final office Action dated Jul. 22, 2022 in U.S. Appl. No. 17/328,346.
U.S. Non-Final office Action dated Nov. 15, 2022 in U.S. Appl. No. 16/447,169.
U.S. Non-Final Office Action dated Apr. 25, 2023 in U.S. Appl. No. 16/550,052.
U.S. Non-Final Office Action dated Mar. 25, 2022, in U.S. Appl. No. 16/550,052.
U.S. Notice of Allowance dated Jan. 9, 2023 in U.S. Appl. No. 17/328,346.
U.S. Notice of Allowance dated Apr. 12, 2023 in U.S. Appl. No. 16/447,169.
US Office Action dated Jan. 25, 2021 in U.S. Appl. No. 16/447,169.
US Office Action dated May 5, 2021 in U.S. Appl. No. 16/550,052.
US Office Action dated Sep. 18, 2020 in U.S. Appl. No. 16/550,052.
U.S. Appl. No. 63/124,673, inventors Tai et al., filed on Dec. 11, 2020.
U.S. Appl. No. 63/146,365, inventors Brown et al., filed on Feb. 5, 2021.
U.S. Appl. No. 63/163,305, inventors Trikha et al., filed on Mar. 19, 2021.
U.S. Appl. No. 63/171,871, inventors Gomez-Martinez et al., filed on Apr. 7, 2021.

(56) References Cited

OTHER PUBLICATIONS

U.S. Appl. No. 63/181,648, inventors Makker et al., filed on Apr. 29, 2021.
U.S. Pat. Appl. No. PCT/US2021/017946, filed on Feb. 12, 2021.
U.S. Appl. No. 63/212,483, inventors Martinson et al., filed on Jun. 18, 2021.
U.S. Appl. No. 63/246,770, Inventors Martinson et al., filed on Sep. 21, 2021.
U.S. Appl. No. 17/791,507, inventors Gopinathanasari et al., filed on Jul. 7, 2022.
U.S. Appl. No. 17/910,722, inventor Trikha et al., filed on Sep. 9, 2022.
U.S. Appl. No. 17/924,105, inventors et al., filed on Nov. 8, 2022.
U.S. Appl. No. 18/028,292, inventors Martinson et al., filed on Mar. 24, 2023.
U.S. Appl. No. 18/042,712, inventors Gupta et al., filed on Feb. 23, 2023.
US Preliminary Amendment dated Apr. 6, 2020 in U.S. Appl. No. 16/550,052.
US Preliminary Amendment dated Nov. 13, 2019 in U.S. Appl. No. 16/447,169.
CA Office Action dated Oct. 11, 2023 in CA Application No. CA3169935.
CA Office Action dated Oct. 25, 2023, in Application No. CA3169929.
CA Office Action dated Sep. 27, 2023, in Application No. CA3103480.
EP Office action dated May 16, 2023, in Application No. EP19745809.4.
IN Office Action dated Sep. 13, 2022, in Application No. IN202037054068.
International Preliminary Report on Patentability and Written Opinion dated Dec. 7, 2023 in PCT Application No. PCT/US2022/030757.
International Preliminary Report on Patentability dated Jun. 22, 2023, in Application No. PCT/US2021/062774.
International Preliminary Report on Patentability dated Oct. 19, 2023, in PCT Application No. PCT/US2022/023605.
International Preliminary Report on Patentability dated Oct. 26, 2023, in Application No. PCT/US2022/024343.
International Preliminary Report on Patentability dated Oct. 26, 2023, in Application No. PCT/US2022/024812.
International Preliminary Reporton Patentability dated Sep. 28, 2023, in PCT Application No. PCT/US2022/020730.
TW Office Action dated Apr. 27, 2023, in application No. TW20220142122 with English translation.
U.S. Notice of Allowance dated Jul. 13, 2023 in U.S. Appl. No. 16/447,169.
U.S. Notice of Allowance dated Sep. 19, 2023, in U.S. Appl. No. 16/550,052.
U.S. Appl. No. 18/037,067, inventors Tai et al., filed on May 15, 2023.
U.S. Appl. No. 18/281,913 inventors Trikha N, et al., filed on Sep. 13, 2023.
U.S. Appl. No. 18/286,521, inventors Rasmus et al., filed on Oct. 11, 2023.
U.S. Appl. No. 18/555, 129, inventors MakkerT, et al., filed on Oct. 12, 2023.
CA Office Action dated Feb. 9, 2024 in CA Application No. 3173471.
CA Office Action dated Feb. 13, 2024 in CA Application No. 3173667.
EP Office Action dated Jan. 19, 2024 in EP Application No. 20746440.5.
International Preliminary Report on Patentability and Written Opinion dated Dec. 21, 2023 in PCT Application No. PCT/US2022/032993.
International Search Report and Written Opinion dated Jan. 15, 2024 in PCT Application No. PCT/US2023/074952.
U.S. Non-Final Office Action dated Feb. 23, 2024 in U.S. Appl. No. 17/313,760.
U.S. Appl. No. 18/565,563, inventors Gomez-Martinez F V, et al., filed Nov. 30, 2023.
U.S. Restriction Requirement dated Jan. 24, 2024 in U.S. Appl. No. 17/612,479.

* cited by examiner

SYSTEMS AND METHODS FOR MANAGING BUILDING WELLNESS

CROSS-REFERENCE TO RELATED APPLICATION

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD OF THE INVENTION

The present invention relates to systems and methods for managing building wellness.

BACKGROUND OF THE INVENTION

Information about building wellness is essential in a world struggling to manage and recover from the global pandemic caused by COVID-19. Such information is critical for tenants to: (i) ensure a healthy environment for employees, so they are productive and feel safe in the office; (ii) respond quickly to crises with staffing processes and policies for protecting employee safety and ensuring business continuity; and (iii) understand building and space performance for real estate leases. Building wellness information is also critical for employees to (i) manage personal safety when planning trips to and from the office, and (ii) enjoy a sense of comfort and safety in knowing that the environmental and wellness conditions of the office are being rigorously monitored.

SUMMARY OF THE INVENTION

In various examples, the systems and methods described herein can be used to obtain and process wellness-related data for a building for the purpose of calculating a wellness index (alternatively referred to as a health index) for the building. The wellness-related data can be or include one or more wellness parameters related to, for example, air and water quality, occupancy, body temperature, reported illnesses, and/or previous building maintenance or cleaning. In general, the wellness index provides an overall measure or indication of a wellness of the building. The wellness index can indicate, for example, how risky it may be from a personal wellness standpoint for a person to enter or spend time in the building. For example, the wellness index can indicate a likelihood that the building may be contaminated with a virus (e.g., a coronavirus) or other pathogen. Additionally, or alternatively, the wellness index can provide an indication of how likely it may be that a person who enters or spends time in the building will be exposed to a virus or other pathogen.

In some implementations, the wellness index and/or supporting data can be made available to one or more occupants of the building (e.g., employees) or people who otherwise visit or enter the building (e.g., vendors, customers, etc.). Such information can be made available through a software application (e.g., installed on user mobile phones, personal computers, etc.), digital signage, text messaging or notifications, a tenant interface, and/or building manager tools. Availability of the wellness index and related data can empower occupants and building staff to make data-driven decisions around managing staff and resources in the context of any wellness risks associated with conditions in the building. For example, the wellness index can be used to facilitate a corrective action to improve the current wellness index or building wellness. Such action can be or include, for example, requiring people to vacate the building or move to specific portions of the building, requiring people to reduce occupancy in the building, requiring use of personal protective equipment, and/or performing maintenance or cleaning on one or more contaminated or damaged building components or areas.

In various examples, the wellness parameters used to calculate the wellness index for a building can include data related to a condition of the building and/or the building s occupants or visitors. The wellness parameters can include, for example, building occupancy data (e.g., a number of occupants and/or a population density for the building), occupant wellness report data (e.g., data indicating one or more occupants is presently sick or recovering from recent illness), air quality data, water quality data (e.g., data describing water quality for a cooling tower), building cleanliness data (e.g.,a length of time since a previous deep cleaning or recent pathogen exposure), occupant body temperature data, historical building wellness index data (e.g.,a rate of change or trend for the wellness index), or any combination thereof. Such data can be collected or obtained from one or more building managers, occupants, medical professionals, cleaning professionals, other personnel, or measurement devices.

The wellness index can be calculated by combining one or more of the wellness parameters. For example, each wellness parameter can be assigned a numerical value (e.g., from 0 to 1, or from −1 to 1) indicating a wellness risk associated with the parameter. For example, if a parameter indicates a wellness risk is high, the value of the parameter can be set to O or −1. Alternatively, if the parameter indicates the wellness risk is low, the value of the parameter can be set to 1. Each wellness parameter can then be assigned a weight, and the wellness index can be calculated as follows:

$$\text{Wellness Index} = W_1 P_1 + W_2 P_2 + \ldots + W_N P_N, \quad (1)$$

where $P_i$ is a wellness parameter $W_i$ is a corresponding weight, and N is the number of wellness parameters. Other methods for calculating the wellness index are contemplated. For example, one or more machine learning models or classifiers can be trained and used to calculate the wellness index. For example, one or more wellness parameters can be provided to a machine learning model as input, and the wellness index can be provided by the machine learning model as output. The machine learning model can be trained to identify building wellness issues using training data that includes, for example, wellness parameters and corresponding values for the wellness index. Additionally, or alternatively, one or more functional forms can be used to combine the wellness parameters (e.g., besides the linear form in equation (1)) and calculate the wellness index. Such functional forms can be or include, for example, non-linear functions, exponential functions, logarithmic functions, quadratic functions, and the like.

Advantageously, the systems and methods described herein can improve accuracy and/or automation of data processing. Data related to building wellness is collected from a variety of sources, including sensors in and around buildings (e.g., body temperature scanners, air quality sensors, security cameras, occupancy sensors, social distancing badges, etc.), push buttons, medical testing labs, and/or information provided by occupants (e.g., through surveys or self-reporting). The systems and methods can aggregate such data in an automated manner to calculate a building wellness index and take corrective action, as needed. Compared to prior approaches, which can rely on manual data collection and analysis, the computer-implemented systems, connected sensors, algorithms, and machine learning techniques described herein are able to achieve a more automated approach for processing data related to building wellness and ensuring that issues related to building wellness are identified and addressed in an efficient and accurate manner.

In a first aspect, the invention relates to a computer-implemented method of managing building wellness. In some embodiments, the method includes the steps of: obtaining wellness parameters for a building (e.g., an office building) having an occupant(s) (e.g., an employee(s)); processing the wellness parameters to determine a current wellness index for the building and, based on the current wellness index, and sending a message regarding the current wellness index to a recipient(s) (e.g., a building occupant), (ii) displaying the current wellness index for a user(s), and/or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

In some implementations, the method may include one or more of the following: building occupancy data may include a number of occupants for the building and/or a population density for the building; occupant wellness report data may include data indicating an occupant(s) is presently sick or recovering from recent illness; water quality data may include data describing water quality for a cooling tower; building cleanliness data may include a length of time since a previous deep cleaning or recent pathogen exposure; historical building wellness index data comprises at least one of a rate of change for the wellness index or a trend for the wellness index.

In some applications, displaying the current wellness index may include presenting the current wellness index on a client device of a user(s) and/or identifying a remediation action(s) may include instructing people to vacate the building, move to a specific portion of the building, use personal protective equipment inside the building, and/or clean an area(s) of the building.

In a second aspect, the invention relates to a system for managing building wellness. In some embodiments, the system includes a computer processor(s) adapted to perform operations. In some embodiments, stored instructions in the computer processor(s) include: obtaining wellness parameters for a building (e.g., an office building) having an occupant(s) (e.g., an employee(s)); processing the wellness parameters to determine a current wellness index for the building and, based on the current wellness index, sending a message including the current wellness index to a recipient(s) (e.g., an occupant(s), displaying the current wellness index for a user(s), and/or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

In some implementations, building occupancy data may include a number of occupants for the building and/or a population density for the building; occupant wellness report data may include data indicating an occupant(s) is presently sick or recovering from recent illness; water quality data may include data describing water quality for a cooling tower; building cleanliness data may include a length of time since a previous deep cleaning or recent pathogen exposure; historical building wellness index data may include a rate of change for the wellness index and/or a trend for the wellness index.

In some applications, displaying the current wellness index may include presenting the current wellness index on a client device of a user(s) and/or identifying the remediation action(s) may include instructing people to vacate the building, move to a specific portion of the building, use personal protective equipment inside the building, and/or clean an area(s) of the building.

In a third aspect, the invention relates to a non-transitory computer-readable medium having instructions stored thereon that, when executed by a computer processor(s), cause the computer processor(s) to perform operations. In some embodiments, the stored instructions include: obtaining wellness parameters for a building (e.g., an office building) having an occupant(s) (e.g., an employee(s)); processing the wellness parameters to determine a current wellness index for the building; and, based on the current wellness index, sending a message including the current wellness index to a recipient(s) (e.g., an occupant(s), displaying the current wellness index for a user(s), or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Terminology

Figure 1:
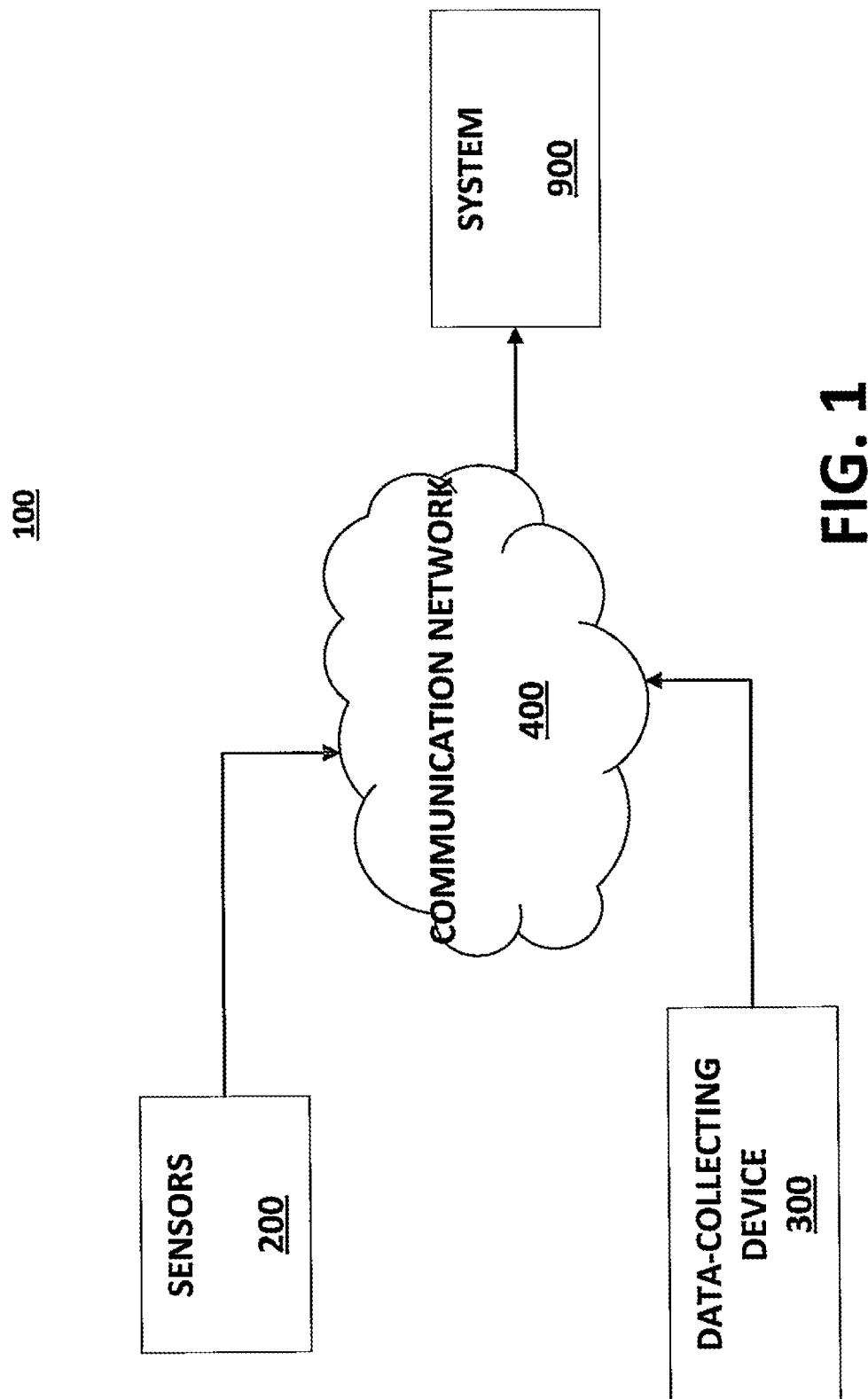
FIG. 1 shows a block diagram of an exemplary architecture for managing building wellness, in accordance with some embodiments of the present invention.

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y") should be understood to mean that one value (X) is within a predetermined range of another value (Y). The predetermined range may be plus or minus 20%, 10%, 5%, 3%, 1%, 0.1%, or less than 0.1%, unless otherwise indicated.

Measurements, sizes, amounts, etc. may be presented herein in a range format. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 10-20 inches should be considered to have specifically disclosed subranges such as 10-11 inches, 10-12 inches, 10-13 inches, 10-14 inches, 11-12 inches, 11-13 inches, etc.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of" or "exactly one of". "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as anon-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Building Wellness Index

Advantageously, the systems and methods described herein are structured and arranged to calculate a building wellness index (BWI) providing a plurality (e.g., four) wellness levels termed "good," "moderate," "use caution," and "alert." Those of ordinary skill in the art can appreciate that the number and names of the wellness levels may vary by implementation and that the following description is meant to be instructive and illustrative of the BWI. In calculating a BWI, assumptions and considerations may include the desire to avoid (i) recommendations that violate any lease and (ii) claims that may directly impact personal and/or individual health decisions. Moreover, the BWI calculated should be (i) based on governmental guidelines when determining any occupancy thresholds and (ii) based on established (e.g., ASHRAE, CDC, EPA, and the like) baselines for any thresholds relating to health and wellness. Furthermore, although all data will be available for use in calculating the BWI, not all data may factor into the risk level calculation.

When the data used to calculate a BWI results in a "good" level, there is deemed no increased health risk to occupants (e.g., tenants, building employees, building visitors, and so forth); hence, occupants are free to enter into and work freely within the building without the need for wearing increased personal protection equipment (PPE), social distancing, or other restrictive practices. Alternatively, when the data used to calculate a BWI results in an "alert" level, conditions within the building are deemed life threatening or, in the alternative, the building must comply with a government "shelter in place" order. Under "alert" conditions, potential occupants (e.g., tenants, building employees, building visitors, and so forth) should avoid coming to the office building and should work from home. The intermediate alert levels stand somewhere between the ideal conditions of "good" and the heightened risk conditions of "alert." Thus, the "moderate" and "use caution" levels reflect a decrease in life threatening conditions and/or government restrictions, resulting in a corresponding decrease in usage limitations and required safety practices for occupants.

In calculating a BWI risk rating, direct, indirect, and other factors may be taken into account. As previously stated, although all data will be available for use in calculating the BWI, not all data may factor into the risk level calculation. Direct factors include data that are direct indicators of a possible risk due to a pathogen (e.g., a virus, such as COVID-19) and are primary contributors to risk level escalation. Indirect factors may indicate overall risk trends or otherwise contribute to possible risk due to a pathogen (e.g., a virus, such as COVID-19) and a secondary contributor(s) to risk level escalation. Other factors that are neither direct nor indirect may have no correlation to possible risk due to a pathogen (e.g., a virus, such as COVID-19); however, they are important to overall wellness and health of building occupants.

Table I provides exemplary risk rate criteria due to direct factors for each of the four wellness levels. In some implementations, these factors may include historic risk, building density, pathogen (e.g., COVID) space testing, reported pathogen (e.g., COVID) cases, and elevated employee temperatures.

TABLE I

LEVEL CRITERIA (DIRECT FACTORS)

| FACTOR | ALERT IF ANY OF THE FOLLOWING ARE TRUE | USE CAUTION IF ANY OF THE FOLLOWING ARE TRUE | MODERATE IF ANY OF THE FOLLOWING ARE TRUE | GOOD IF ALL OF THE FOLLOWING ARE TRUE |
|---|---|---|---|---|
| Historic Risk | NIA | 24 hours < since ALERT tatus | 24 hours < since USE CAUTION status | >24 hours since MODERATE status |
| Building Density | "shelter in place" or "stay at home" order from CDC or government agency | Building density < 110% of target and government agency recommendation in effect | Building density > 110% of target and government agency recommendation in effect | No government agency recommendation in effect |
| Pathogen (COVID) Space Testing | | 3 samples < detected in the last week | Between 1 and 3 samples detected in the last week | More than one week since last sample was discovered. |
| Reported Pathogen (COVID) Cases | | 1% of building population < reported with pathogen in last 2 weeks | 1 or more cases of pathogen reported in the last two weeks | No cases of highly infectious diseases reported in the last two weeks |
| Elevated Employee Temperatures | | 1 standard deviation < above monthly average baseline | | Monthly average baseline of elevated temperature employees≤ |

Table II provides exemplary risk rate criteria due to other factors for each of the four levels. In some implementations, these factors may include carbon monoxide (CO) levels, levels of particulate matter (PM1O), ozone levels, volatile organic compounds (VOC) levels, formaldehyde levels, and legionella levels (for buildings that draw potable water from cooling water towers). The Table II factors deal more with the environment and how it may affect human beings as opposed to factors that affect the building itself.

TABLE II

LEVEL CRITERIA (OTHER FACTORS)

| FACTOR | ALERT IF ANY OF THE FOLLOWING ARE TRUE | USE CAUTION IF ANY THREE (3) OF THE FOLLOWING ARE TRUE | MODERATE IF ANY THREE (3) OF THE FOLLOWING ARE TRUE | GOOD |
|---|---|---|---|---|
| CO (in 8 hours) | ≥12.4 ppm | 9.5< ≤12.4 ppm | 4.4 ppm< ≤9.4 ppm | |
| PMIO (in 24 hours) | >255 µg/m3 | 155 µg/m3< ≤254 µg/m3 | 54 µg/m3< ≤154 µg/m3 | |
| OZONE (in 8 hours) | 0.086 ppm< ≤0.105 ppm | 0.070 ppm< ≤0.086 ppm | 0.054 ppm< ≤0.070 ppm | |
| VOC | >1000 µg/m3 | 500 µg/m3< ≤I000 µg/m 3 | 500 µg/m3< | |
| Formaldehyde | ≥5 ppm (in 8 hours) | | 0.027 ppm< | |
| Legionella | YES | | | NO |

Table III provides exemplary risk rate criteria due to indirect factors for each of the four levels. These indirect factors may include, for example, carbon dioxide levels (CO2), humidity, levels of particulate matter (PM2-5), and employee absenteeism. The Table III factors deal more with the environment and how it may affect human beings.

TABLE III

LEVEL CRITERIA (INDIRECT FACTORS)

| FACTOR | ALERT IF ANY OF THE FOLLOWING ARE TRUE | USE CAUTION IF ANY OF THE FOLLOWING ARE TRUE | MODERATE IF ANY OF THE FOLLOWING ARE TRUE | GOOD IF ANY OF THE FOLLOWING ARE TRUE |
|---|---|---|---|---|
| CO2 | | | >10% above (ambient) outside air CO2 levels | <10% below (ambient) outside air CO2 levels |
| Humidity | | | <40% | 40%< <60% |
| PM2-5 (in 24 hours) | >55.4 μg/m3 | 35.4 μg/m3< ≤55.4 μg/m | | ≤35.4 μg/m3 |
| Employee Absenteeism | | | Illness-related employee absenteeism has trended upward for 3 days | Illness-related employee absenteeism has remained stable or decreased for at least 3 days |

System Architecture

Referring to FIG. 1, an exemplary architecture of an embodiment of a system 100 for managing building wellness is shown. In some implementations, the system 100 includes a plurality of sensors 200 and/or data-collecting devices 300, as well as a computer-based system 900 that is configured to calculate a wellness (or health) index using, inter alia, data from the plurality of sensors 200 and/or data-collecting devices 300. Although the term "devices" connotes a mechanical means, those of ordinary skill in the art can appreciate that "devices" may also include a survey, a questionnaire, computer input, and so forth.

A communication network 400 enables the transfer of (e.g., communication) signals and data between the computer-based system 900 and the sensors 200 and data-collecting devices 300, such that data collected by the sensors 200 and data-collecting devices 300 may provide insight as to what is occurring, what may be occurring, and/or what is likely to occur within the (e.g., office) building. Moreover, these data and insights may be used so that remedial, preventive, and/or other action may be taken to improve the quality of life within the building. In some variations, such action may be communicated (e.g., via email, text message, phone call, and the like) to individuals or building departments responsible for effecting the remedial action.

In some embodiments, the computer-based system 900 includes stored instructions for operations that, initially, may include obtaining wellness parameters for a (e.g., office) building having occupants (e.g., employees and/or visitors). Wellness parameters may include, for the purpose of illustration rather than limitation: building occupancy data, occupant wellness report data, air quality data, water quality data, building cleanliness data, occupant body temperature data, historical building wellness index data, and/or any combination thereof. Building occupancy data may include a number of occupants for the building, which can include a floor-by-floor and a room-by-room assessment and/or a population density for the building. Occupant wellness report data may include data indicating one or more occupants is presently sick or recovering from recent illness. Water quality data may include data describing water quality for a cooling tower. Building cleanliness data may include a length of time since a previous deep cleaning or recent pathogen exposure. Historical building wellness index data may include a rate of change for the wellness index and/or a trend for the wellness index.

The computer-based system 900 may also include stored instructions for processing the wellness parameters to determine a current wellness (or health) index for the building as indicia of the risk of being exposed to a pathogen (e.g., a virus, COVID-19, and so forth); and, based on the current wellness index, sending a message to a recipient who is designated to take some action to address a deficiency in the current wellness index. For example, sending a message may include sending the current wellness index to a recipient(s), displaying the current wellness index for a user(s), and/or identifying a remediation action(s) to improve the current wellness index. The current wellness index provides an indication of a risk of being exposed to a pathogen (e.g., a virus) inside the building. Displaying the current wellness index may include presenting the current wellness index on a client device of a user(s), while identifying the remediation action(s) may include instructing people to vacate the building, move to a specific portion of the building, use personal protective equipment inside the building, and/or clean one or more areas of the building.

For example, for the purpose of determining building occupancy (including occupancy on a floor-by-floor and/or room-by-room basis), building density, building foot traffic, tenant usage, and tenant engagement, the sensors 200 and data-collecting devices 300 may include threshold counters (e.g., at points of access and egress) for counting and recording the number of building occupants (and visitors) that have entered/exited the building, closed-circuit television (CCTV) for identifying discrete building occupants who have entered/exited the building, and/or individual access badges that may be scanned automatically or manually when the building occupant or visitor(s) enters/exits the building. In addition to, for example, predicting future occupancy, ascertaining foot traffic trends, and managing elevator queuing, such data may be used, inter alia, to ensure that the number of personnel within the building does not exceed government (e.g., health and safety) guidelines and/or protocols.

Such data may also be used to estimate optimal cleaning scheduling and staffing so that janitorial and cleaning staff operations may be adjusted. For example, under Use Caution, Moderate, and/or Good levels, janitorial and custodial staff may be used to continuously clean all high touch areas and high touch points, for example, in the building lobby and common areas. For the purpose of illustration rather than limitation, high touch points may include door handles, turnstiles, lobby desks, elevator buttons, sneeze guards, revolving doors, and the like. Furthermore, when conditions regarding public health and safety present an elevated risk (e.g., Use Caution level), janitorial and custodial personnel may be directed to perform additional cleaning, targeting paths of occupant travel and common areas in line with CDC guidelines. Sensors 200 and data-collecting devices 300 installed in building restrooms may also include push buttons by which users of the facilitates may indicate facility use, so that restocking of restroom supplies and periodic cleaning may be tailored to such use. Sensors 200 and data-collecting devices 300 may also be installed at other building amenity centers (e.g., snack bar, cafeteria, and so forth) to provide insight into amenity usage from which cleaning schedules may be optimized.

For the purpose of optimizing workspace needs and trends, sensors 200 and data-collecting devices 300 may include (e.g., floor and/or room) occupancy sensors by which insights into office assignment and meeting space needs and utilization, into employee space needs, into employee work habits, into team collaboration, into employee interaction, and the like may be gathered. Amenity occupancy sensors may also provide data for evaluating and optimizing amenity needs and utilization.

For the purpose of providing insight into building and/or occupant wellness and/or occupant comfort, the sensors 200 and data-collecting devices 300 may include (e.g., indoor and/or outdoor) air quality (AQ) sensors, (e.g., non-invasive) elevated body temperature sensors, and the like. AQ sensors may include humidity sensors, which may be used, inter alia to maintain a humidity level within the building that may suppress pathogen transmission. For example, non-invasive, high-occupancy body temperature scanners may be installed in the building lobby and all occupants and visitors may be required to pass through. In addition to identifying individual occupants whose health may jeopardize that of other building occupants, such data may be used, for example, to determine when to replace and/or recalibrate AQ sensors, when to mitigate AQ events, and so forth. Social distancing badges may also be used to track contact between occupants.

In some implementations, a medical screening or care site and/or a medical testing lab may be included in the building. For example, in addition to wearing facial masks in accordance with CDC guidelines in all building common areas, visitors and occupants may be required to complete a (e.g., COVID-related) building access questionnaire before accessing the building. Building common areas may include, for the purpose of illustration rather than limitation, lobbies, elevators, stairwells, bathrooms, amenity centers, and so forth. Facial masks, protective gloves, hand sanitizer, and the like may also be provided at the medical screening or care site. In some instances, pathogen (e.g., COVID) testing may be performed and/or vaccinations may be provided.

In some implementations, occupants may be provided with a tenant engagement application ("app"). In some embodiments, the tenant engagement app is a mobile application used by occupants of the building to perform daily activities, including completion of a health attestation. The app also provides mechanisms to publish surveys to the occupants to get their feedback on conditions within the building, such as overall cleanliness. Data from the tenant engagement app, as well as health attestation, surveys, or other employee activity, may be used as inputs for the algorithm.

Public data sets may also be included in the logarithm. For the purpose of illustration rather than limitation, public data sets may include local hospitalization rates for flu-like symptoms, COVID cases in the region, and public mobility data to ascertain local crowding and density.

Sensors 200 and data-collecting devices 300 may also include sensors that, conventionally, are included with building systems for the purpose, for example, of monitoring some aspect of the building. Among these building system sensors 200 and data-collecting devices 300 are utility meters, water and air temperature sensors, furnace or boiler sensors, building work orders, and the like. Such data may provide insight into energy usage and energy cost optimization for the purpose of monitoring energy performance. Such data may also provide indicia of general building and/or building plant preventive maintenance needs that may be addressed prior to an emergency repair.

Figure 2:
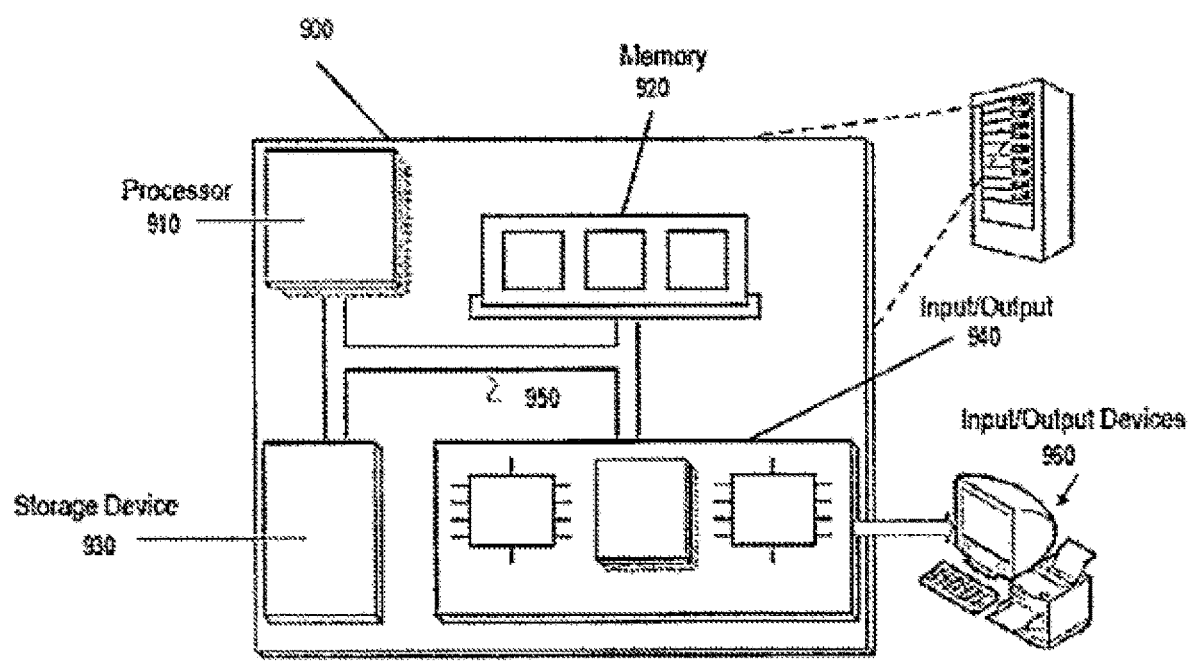
FIG. 2 shows a block diagram of an exemplary computer system for managing building wellness, in accordance with some embodiments of the present invention.

FIG. 2 shows a block diagram of an exemplary computer system 900 that may be used in implementing the technology described in this document. General-purpose computers, network appliances, mobile devices, or other electronic systems may also include at least portions of the system 900. In some implementations, the system 900 may include a processor 910, a memory 920, a storage device 930, and an input/output device 940. Each of the components 910, 920, 930, and 940 may be interconnected, for example, using a system bus 950.

Advantageously, the (e.g., single- or multi-threaded) processor 910 is capable of processing instructions for execution within the system 900. In some variations, these instructions may be stored in the memory 920 and/or on the storage device 930.

The memory 920 stores information within the system 900. In some implementations, the memory 920 may be a non-transitory computer-readable medium. In some implementations, the memory 920 may be a volatile memory unit. In some implementations, the memory 920 may be a non-volatile memory unit.

The storage device 930 is capable of providing mass (e.g., data) storage for the system 900. In some implementations, the storage device 930 may be a non-transitory computer-readable medium. In various different implementations, the storage device 930 may include, for example, a hard disk device, an optical disk device, a solid-date drive, a flash drive, or some other large capacity storage device. For example, the storage device may store long-term data (e.g., database data, file system data, etc.).

In some embodiments, the input/output device 940 provides input/output operations for the system 900. For example, in some implementations, the input/output device 940 may include one or more of: a network interface device, e.g., an Ethernet card; a serial communication device, e.g., an RS-232 port; and/or a wireless interface device, e.g., an 802.11 card; a 3G wireless modem, and/or a 4G wireless modem. In some implementations, the input/output device 940 may include driver devices configured to receive input data and to send output data to other input/output devices 960, e.g., keyboard, printer, and display devices. In some examples, mobile computing devices, mobile communication devices, and other devices may be used.

In some implementations, at least a portion of the approaches described above may be realized by instructions that, upon execution, cause one or more processing devices to carry out the processes and functions described above. Such instructions may include, for example, interpreted instructions such as script instructions, or executable code, or other instructions stored in a non-transitory computer readable medium. The storage device 930 may be implemented in a distributed way over a network, for example as a server farm or a set of widely distributed servers, or may be implemented in a single computing device.

Although an exemplary processing system 900 has been described in FIG. 1, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term system may encompass all kinds of apparatuses, devices, and machines for processing data, including, for the purpose of illustration rather than limitation, a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, an engine, a pipeline, a module, a software module, a script, or code) can be written in any form of programming language, including compiled or interpreted languages, or declarative or procedural languages, and it can be deployed in any form, including as a stand-alone program or as a module, component, sub-routine, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may also be deployed to be executed on a single computer or on multiple computers that, for example are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as special purpose logic circuitry, e.g., an FPGA (field programmable gate ray)or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from and/or transfer data to, one or more mass storage devices for storing data, e.g., magnetic, magneto-optical disks, or optical disks. However, a computer need not have such devices. Moreover, a computer may be embedded in another device, e.g., a mobile or cellular telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks magneto-optical disks and CD-ROM and DVD-ROM disks. The processor and the memory can be supplemented by, or incorporated in, special purpose logic circuit.

To provide for interaction with a user, embodiments of the subject matter described in this specification may be implemented on a computer having a display device, e.g., a CRT (cathode ray tube) or LCD (liquid crystal display) monitor, for displaying information to the user, as well as a keyboard and a pointing device, e.g., a mouse or a trackball, by which the user can provide input to the computer. Other kinds of devices can be used to provide for interaction with a user as well for example, feedback provided to the user can be any form of sensory feedback, e.g., visual feedback, auditory feedback, or tactile feedback and input from the user can be received in any form, including acoustic, speech, or tactile input. In addition, a computer can interact with a user by sending documents to and receiving documents from a device that is used by the user; for example, by sending Web pages to a Web browser on a user s user device in response to requests received from the Web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Although this specification contains many specific implementation details, these details should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

The invention claimed is:

1. A method, implemented by a computer system associated with a building, the method comprising the computer system:
  collecting, from a plurality of sensors disposed in and/or around the building and communicatively coupled with the computer system, data related to the building, wherein the data comprises carbon dioxide levels, humidity levels, particulate matter levels, volatile organic compound (VOC) levels, and air temperature levels;
  determining, based on processing the data received from the plurality of sensors, a current health index related to the building based on aggregating a plurality of parameters that are each assigned a weight of a plurality of weights, wherein:
    the plurality of parameters comprises a carbon dioxide parameter based on the collected carbon dioxide levels, a humidity parameter based on the collected humidity levels, a particulate matter parameter based on the collected particulate matter levels, a VOC parameter based on the collected VOC levels, and an air temperature parameter based on the collected air temperature levels,
    the assigning comprises assigning the carbon dioxide parameter a first weight, assigning the humidity parameter a second weight, assigning the particulate matter parameter a third weight, assigning the VOC parameter a fourth weight, assigning the air temperature parameter a fifth weight, and
    the first weight is different than at least one of the other weights;
  identifying, based at least in part on the determined current health index, one or more remediation actions to improve the determined current health index; and
  communicating the determined current health index and the one or more remediation actions to at least one recipient and/or to at least one or more occupants of the building.

2. The method of claim 1, wherein:
  the plurality of parameters further includes an occupancy parameter based on occupancy related data; and
  the assigning further includes assigning the occupancy parameter a sixth weight.

3. The method of claim 2, wherein the occupancy related data comprises a number of occupants in the building, a number of occupants in a floor of the building, a number of occupants in a room of the building, a population density for the building, an occupancy threshold for the building, or a combination thereof.

4. The method of claim 1, wherein:
  the plurality of parameters further includes a historical data parameter based on a rate of change and/or a trend of the health index; and
  the assigning further includes assigning the historical data parameter a sixth weight.

5. The method of claim 1, wherein:
  the data further comprises ozone levels and formaldehyde levels;
  the plurality of parameters further comprises an ozone parameter based on the collected ozone levels, a formaldehyde parameter based on the collected formaldehyde levels; and
  the assigning further comprises assigning the ozone parameter a sixth weight and assigning the formaldehyde parameter a seventh weight.

6. The method of claim 1, wherein:
  the data further comprises carbon monoxide levels;
  the plurality of parameters further comprises a carbon monoxide parameter based on the collected carbon monoxide levels; and
  the assigning further comprises assigning the carbon monoxide a sixth weight.

7. The method of claim 1, wherein:
  the plurality of parameters further includes an energy usage parameter based on energy related data; and
  the assigning further includes assigning the energy usage parameter a sixth weight.

8. The method of claim 7, wherein the energy related data comprises data from a utility meter, a water temperature sensor, a furnace sensor, a boiler sensor, or a combination thereof.

9. The method of claim 1, wherein the particulate matter levels comprise PM2.5 and PM10 particulate matter.

10. The method of claim 1, wherein the determining further includes assigning each parameter with a numerical value.

11. A system comprising:
a computer system; and
a plurality of sensors disposed in and/or around a building and communicatively coupled with the computer system, the computer system configured to perform operations comprising:
collecting, from the plurality of sensors, data related to the building, wherein the data comprises carbon dioxide levels, humidity levels, particulate matter levels, volatile organic compound (VOC) levels, and air temperature levels;
determining, based on the data received from the plurality of sensors, a current health index related to the building based on aggregating a plurality of parameters that are each assigned a weight of a plurality of weights, wherein:
the plurality of parameters comprises a carbon dioxide parameter based on the collected carbon dioxide levels, a humidity parameter based on the collected humidity levels, a particulate matter parameter based on the collected particulate matter levels, a VOC parameter based on the collected VOC levels, and an air temperature parameter based on the collected air temperature levels,
the assigning comprises assigning the carbon dioxide parameter a first weight, assigning the humidity parameter a second weight, assigning the particulate matter parameter a third weight, assigning the VOC parameter a fourth weight, assigning the air temperature parameter a fifth weight, and
the first weight is different than at least one of the other weights;
identifying, based at least in part on the determined current health index, one or more remediation actions to improve the determined current health index; and
communicating the determined current health index and the one or more remediation actions to at least one recipient and/or to at least one or more occupants of the building.

12. The system of claim 11, wherein:
the plurality of parameters further includes an occupancy parameter based on occupancy related data; and
the assigning further includes assigning the occupancy parameter a sixth weight.

13. The system of claim 12, wherein the occupancy related data comprises a number of occupants in the building, a number of occupants in a floor of the building, a number of occupants in a room of the building, a population density for the building, an occupancy threshold for the building, or a combination thereof.

14. The system of claim 11, wherein:
the plurality of parameters further includes a historical data parameter based on a rate of change and/or a trend of the health index; and
the assigning further includes assigning the historical data parameter a sixth weight.

15. The system of claim 11, wherein:
the data further comprises ozone levels and formaldehyde levels;
the plurality of parameters further comprises an ozone parameter based on the collected ozone levels, a formaldehyde parameter based on the collected formaldehyde levels; and
the assigning further comprises assigning the ozone parameter a sixth weight and assigning the formaldehyde parameter a seventh weight.

16. The system of claim 11, wherein:
the data further comprises carbon monoxide levels;
the plurality of parameters further comprises a carbon monoxide parameter based on the collected carbon monoxide levels; and
the assigning further comprises assigning the carbon monoxide a sixth weight.

17. The system of claim 11, wherein:
the plurality of parameters further includes an energy usage parameter based on energy related data; and
the assigning further includes assigning the energy usage parameter a sixth weight.

18. The system of claim 17, wherein the energy related data comprises data from a utility meter, a water temperature sensor, a furnace sensor, a boiler sensor, or a combination thereof.

19. The system of claim 11, wherein the particulate matter levels comprise PM2.5 and PM10 particulate matter.

20. The system of claim 11, wherein the determining further includes assigning each parameter with a numerical value.

* * * * *